(12) United States Patent
Ogasawara

(10) Patent No.: US 8,715,182 B2
(45) Date of Patent: May 6, 2014

(54) ULTRASONIC IMAGING APPARATUS AND STRESS ECHO BROWSING APPARATUS

(75) Inventor: Yoichi Ogasawara, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1163 days.

(21) Appl. No.: 12/336,848

(22) Filed: Dec. 17, 2008

(65) Prior Publication Data

US 2009/0163813 A1   Jun. 25, 2009

(30) Foreign Application Priority Data

Dec. 25, 2007  (JP) ................................. 2007-331893

(51) Int. Cl.
*A61B 8/00* (2006.01)

(52) U.S. Cl.
USPC .......................................... 600/437; 600/438

(58) Field of Classification Search
USPC ................................................ 600/437–438
See application file for complete search history.

(56) References Cited

U.S. PATENT DOCUMENTS

| | | | | |
|---|---|---|---|---|
| 6,454,712 | B1 * | 9/2002 | Oonuki | 600/437 |
| 6,458,081 | B1 * | 10/2002 | Matsui et al. | 600/437 |
| 6,503,203 | B1 * | 1/2003 | Rafter et al. | 600/458 |
| 2004/0267122 | A1 * | 12/2004 | Nadadur et al. | 600/440 |
| 2005/0049493 | A1 * | 3/2005 | Kerby et al. | 600/437 |
| 2005/0059876 | A1 * | 3/2005 | Krishnan et al. | 600/407 |

FOREIGN PATENT DOCUMENTS

| | | |
|---|---|---|
| JP | 5-237100 A | 9/1993 |
| JP | 8-623 A | 1/1996 |
| JP | 2003-265479 A | 9/2003 |
| JP | 2004-133887 A | 4/2004 |
| JP | 2005-218713 A | 8/2005 |
| JP | 2006-26151 | 2/2006 |
| JP | 2006-26256 | 2/2006 |
| JP | 2006-197967 A | 8/2006 |
| JP | 2008-136867 | 6/2008 |

OTHER PUBLICATIONS

Yao S, Qureshi E, Sherrid MV, and Chaudrhy FA. Practical applications in stress echocardiography. J Am Coll Cardiol. 2003; 42(6): 1084-1090.*
Japanese Office Action issued Sep. 4, 2012 in Patent Application No. 2007-331893.

* cited by examiner

*Primary Examiner* — Peter Luong
(74) *Attorney, Agent, or Firm* — Oblon, Spivak, McClelland, Maier & Neustadt, L.L.P.

(57) ABSTRACT

In plural types of stress echocardiographies, every time a single type of stress or plural types of stresses are applied to a site in plural examination stages for the respective types, a data acquiring part transmits ultrasonic waves to a subject of a data acquisition target, and when reflected waves are received, values of plural types of parameters signifying the state of the site of the subject are obtained. Subsequently, when receiving a request to browse the examination results by designation of the type of stress echocardiography through an operation part, a display controller reads out, from the storage, the values of the parameters of the stress echocardiography of the designated type and displays a list of the values of the parameters on a graphic with one item as the types of the parameters and the other item as the respective examination stages of the designated stress examination.

9 Claims, 6 Drawing Sheets

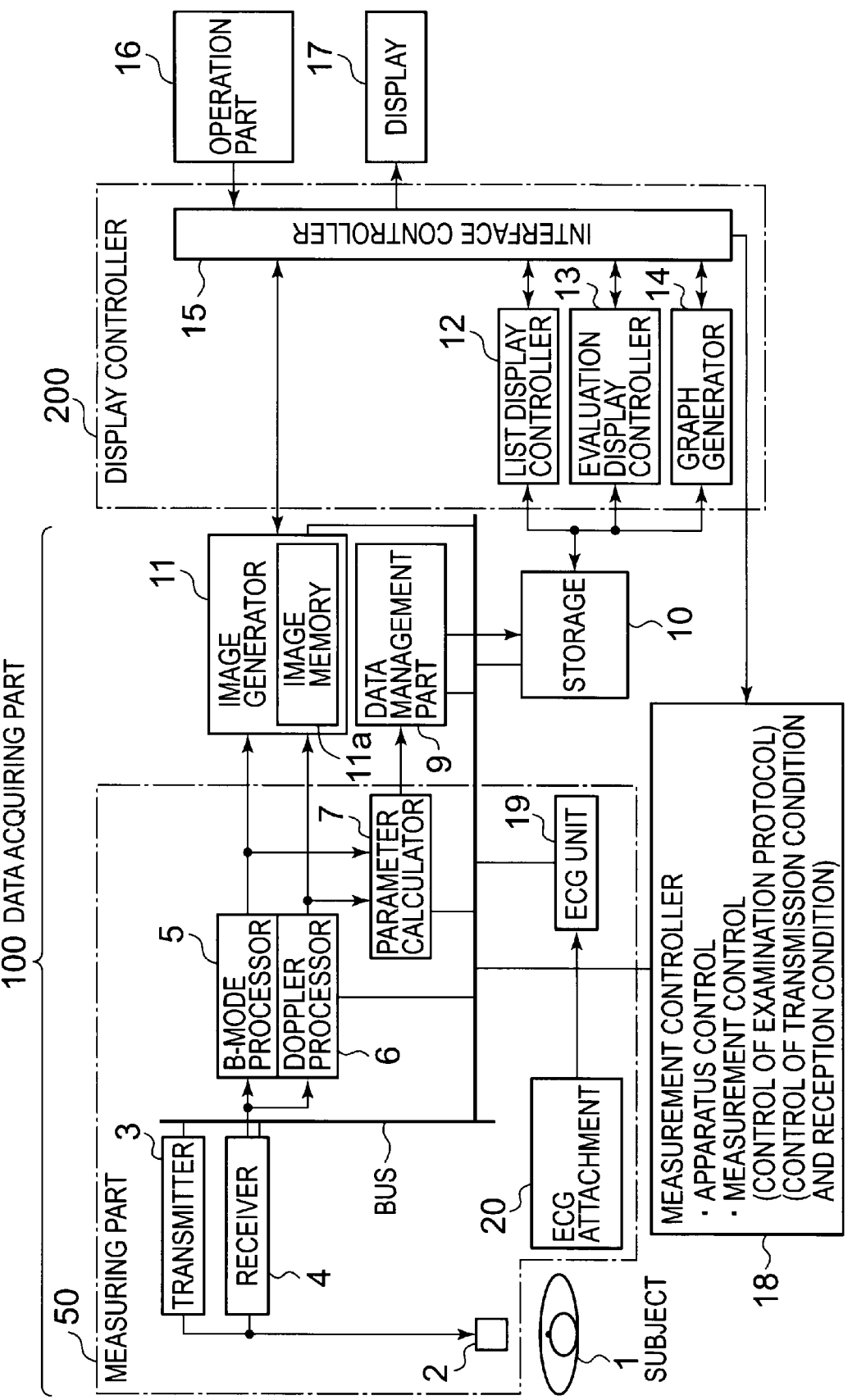

FIG. 2

MEASUREMENT CONTROLLER EXECUTES PARAMETER CALCULATOR MEASURES
BY INSTRUCTION FROM OPERATION PART

EXAMINATION
├─ NORMAL EXAMINATION    (PARAMETER 00-P1、 00-P2、 ‥)
├─ STRESS ECHOCARDIOGRAPHY
├─ EXAMINATION PROCEDURE A
│   ├─ PHASE A1    (PARAMETER A1-P1、 A1-P2、 ‥)
│   ├─ PHASE A2    (PARAMETER A2-P1、 A2-P2、 ‥)
│   │   ─────
│   └─ PHASE An    (PARAMETER An-P1、 An-P2、 ‥)
├─ EXAMINATION PROCEDURE B
│   ├─ PHASE B1    (PARAMETER B1-P1、 A1-P2、 ‥)
│   ├─ PHASE B2    (PARAMETER B2-P1、 B2-P2、 ‥)
│   │   ─────
│   └─ PHASE Bm    (PARAMETER Bm-P1、 Bm-P2、 ‥)
└─ EXAMINATION PROCEDURE C
    ├─ PHASE C1    (PARAMETER C1-P1、 C1-P2、 ‥)
    ├─ PHASE C2    (PARAMETER C2-P1、 C2-P2、 ‥)
    │   ─────
    └─ PHASE Ck    (PARAMETER Ck-P1、 Ck-P2、 ‥)

FIG. 3

NORMAL MEASUREMENT DISPLAY TAG 001

STRESS ECHO DISPLAY TAG 002

COLOR BAR INDICATING VARIATION 004 RATIO OF MEASUREMENT VALUE

PULL-DOWN MENU FOR SELECTING PROTOCOL OF STRESS ECHO 003

CHECK BOX FOR SELECTING MEASUREMENT PARAMETER FOR GRAPH DISPLAY 006

MEASUREMENT VALUE DISPLAY AREA OF "MEASUREMENT PARAMETER" TO "PHASE" 007

005 PHASE

Measure | Stress

Cardiac ▼

Protocol_A ▼

A/O The report shows averaged value. Check all data.   ◄ 1/2 ►

— LV MOD Simpson

| | | Rest | 10 mcg | 20 mcg |
|---|---|---|---|---|
| EDV | mL | 132.5 | 101.3 | 78.6 |
| ESV | mL | 16.1 | 21.4 | 38.7 |
| SV | mL | 116.4 | 79.9 | 39.9 |
| CO | L/min | 6.984 | 6.632 | 2.913 |
| EF | % | 87.8 | 78.9 | 50.8 |
| LVLd Diff | % | 6.2 | −5.3 | −19.1 |
| LVLs Diff | % | 5.7 | 23.2 | −25.2 |
| LVAd2 | cm2 | 33.54 | 27.83 | 24.93 |
| LVLd2 | mm | 72.3 | 79.5 | 85.3 |
| EDV2 | mL | 142.2 | 90.5 | 75.1 |
| LVAs2 | cm2 | 8.50 | 8.39 | 17.87 |
| LVLs2 | mm | 52.9 | 46.9 | 81.7 |
| ESV2 | mL | 13.2 | 14.8 | 36.1 |

Comment

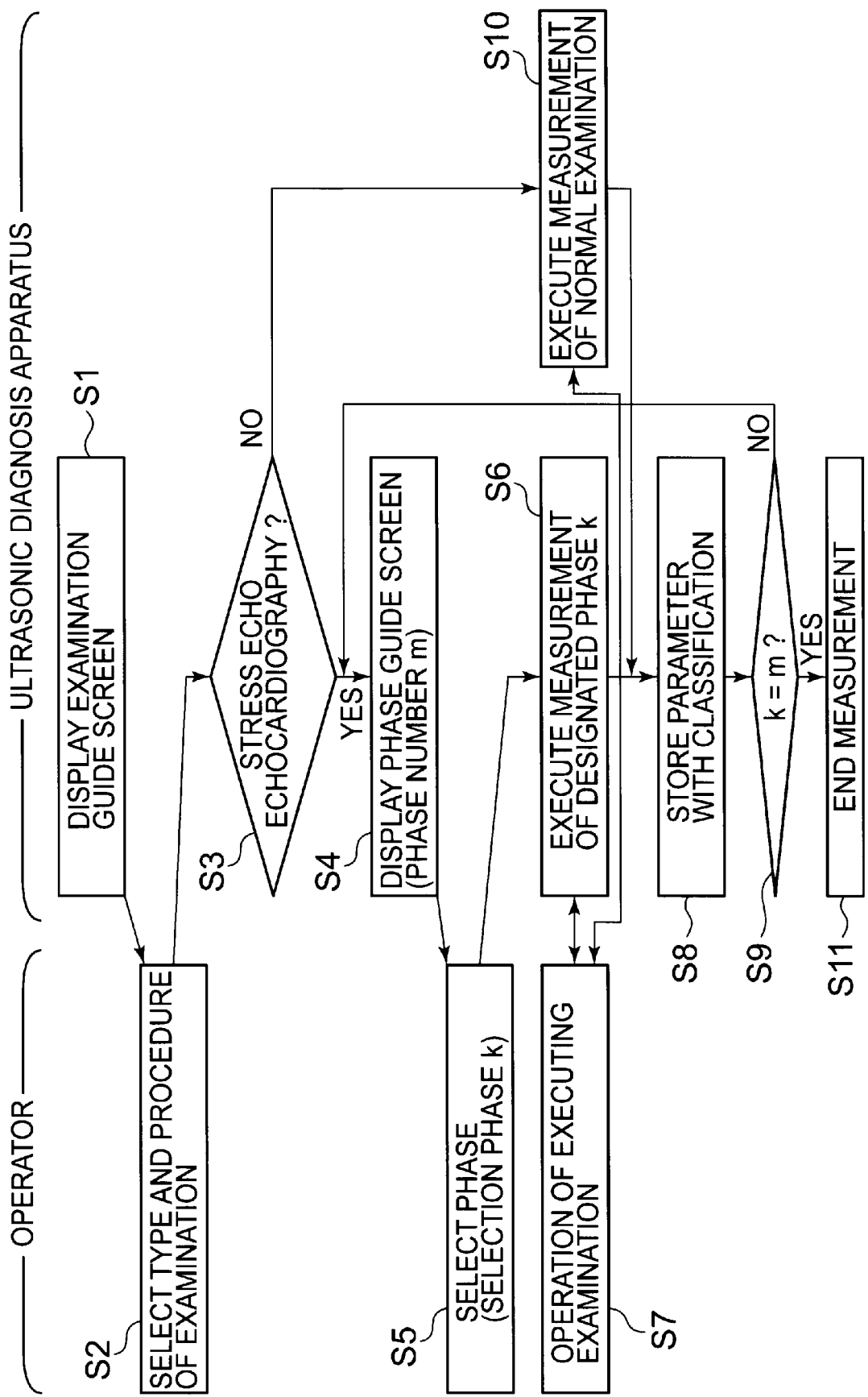

ULTRASONIC IMAGING APPARATUS AND STRESS ECHO BROWSING APPARATUS

BACKGROUND OF THE INVENTION

1. Field of the Invention

The present invention relates to an ultrasonic imaging apparatus that transmits ultrasonic waves to a subject and receives the reflected waves to measure the state of a site of the subject, and also relates to a stress echo browsing apparatus.

The present invention particularly relates to a technology that allows an ultrasonic imaging apparatus configured to change the magnitude of a load (stress, referred to as "load" hereinafter) in a plurality of examination stages to apply to a site of a subject in a plurality of types of stress echocardiographies and configured to measure the state of the site by ultrasonic waves every time applying the load, to acquire a plurality of types of parameters signifying the state of the site in each of the examination stages, store the plurality of types of parameters in categories and easily recognize the change of the parameters in the above measurement.

2. Description of the Related Art

For example, in a stress echocardiography, regarding deterioration of the cardiac function that does not appear in a normal resting state, an ischemic state is generated by applying a load to a heart through an exercise or with a medical agent. Since changes are thereby caused in cardiac ventricles or atriums, particularly in systolic functions or diastolic functions of the left ventricle, it is possible to diagnose constructed sites of blood vessels or regions with deteriorated heart functions (refer to Japanese Unexamined Patent Application Publication JP-A 2006-26151). Furthermore, in order to diagnose the degree of seriousness, the state of the load on the heart is set in stages, which are referred to examination stages, phases, or stages (hereinafter referred to as "phases").

In a diagnosis, the wall motion of a heart is observed or numerically analyzed in real time or with moving images, and the amount of change thereof is evaluated qualitatively and quantitatively.

The numerically analyzed evaluation is conventionally performed on the entire heart or a local part thereof by a method of directly analyzing the motion of a heart, measuring the ventricular volume or the rate of change, or analyzing the blood flow velocity.

In an ultrasonic imaging apparatus (e.g., JP-A 2006-26151), a load is applied to a site while the magnitude thereof is changed in each of a plurality of phases to perform a stress echocardiography. As described in JP-A 2006-26151, the load is, for example, an exercise load and a dobutamine stress. As a typical example of the stress echocardiography based on the exercise load, measurements are executed on a site in three phases, i.e., "before loading," "during loading (at peak load)" and "after loading (recovery)." Furthermore, as a typical example of the stress echocardiography based on the dobutamine stress, measurements are executed on a site in six phases, i.e., "before loading," "10γ loading," "20γ loading," "30γ loading," "40γ loading (at peak load)" and "after loading (recovery)." The number of the phases is not limited by these examples, but the minimum number of the phases in the stress echocardiography is two phases, i.e., before loading and during loading (e.g., peak load).

Then, the ultrasonic imaging apparatus analyzes the motion or strain at a local site in a site image acquired with ultrasonic waves at the time of measurement of each phase, and calculates the values of a plurality of types of parameters signifying the state of the site. In other words, the values of a plurality of types of parameters relating to the motion or strain at the local site are calculated for each phase. Then, such a comparison of obtaining the difference of parameter values of adjacent phases is performed, and data indicating the motion state of the local site is acquired.

In the abovementioned conventional art, when a single type of stress echocardiography is executed, the parameter in each phase is obtained to calculate the amount of change. Then, a list of examination results of the type of stress echocardiography is displayed or outputted.

However, after the stress echocardiography is finished or when it is desired to interpret images to create a report on another day, it is difficult to, e.g., quantitatively grasp the amount of change in Phases 4 through 6 with reference to Phase 2 from the examination results of the stress echocardiography of Phases 1 through 6 under Dobutamine stress A. In other words, the apparatus is not configured to individually output the parameters from the examination results, and therefore, it is impossible to, e.g., derive the parameter of Phase 2 under Dobutamine stress A.

As a result, in the abovementioned conventional art, it is difficult to recognize or visually recognize the amount of change in a desired format with regard to a specific type of parameter.

SUMMARY OF THE INVENTION

An object of the present invention is to provide an ultrasonic imaging apparatus and a stress echo browsing apparatus, which make it possible to quantitatively recognize or visually recognize the amount of change in the state of a site based on the examination results after a stress echocardiography, for example, even when a report, etc., is created after the stress echocardiography is finished.

A first aspect of the present invention provides an ultrasonic imaging apparatus having: a data acquiring part configured to transmit ultrasonic waves to a subject and receive the reflected waves to obtain values of a plurality of types of parameters signifying a state of a site of the subject; and a controller configured to control the data acquiring part to acquire values of respective types of parameters by, in a plurality of types of stress echocardiographies, applying stress corresponding to one type or the plurality of types to the site in a plurality of examination stages for each of the types, and applying no stress in a normal examination, the ultrasonic imaging apparatus comprising: a storage configured to store the values of the respective parameters acquired by the data acquiring part in the stress echocardiographies so as to be identifiable by the types of the stress echocardiographies, by the types of the parameters, and by the examination stages; a display; an operation part; and a display controller having a list display controller configured to, when a type of the stress echocardiography is designated through the operation part and a request for browsing an examination result is received, read out the values of the parameters of the designated type of stress echocardiography from the storage, and display a list of the values of the parameters on a graphic in which one item is the type of the parameters and the other item is each of the examination stages of the designated stress echocardiography.

According to the first aspect, the examination results (parameter values) are classified by the type of stress echocardiography, by the phase and by the type of parameter or provided with tags (identifiers) when stored, so that it is possible to read out and use them later.

Furthermore, on the display, the parameter values are displayed in a table format in which one item takes the types of parameters and the other item takes the respective phases of loads, so that it is possible to quantitatively recognize the change in the state of the site.

Further, in a second aspect of the present invention, in the ultrasonic imaging apparatus according to the first aspect: the display controller includes an evaluation display controller that stores, for each of the types of the parameters, at least three of a standard range, an over range exceeding the standard range and an under range below the standard range as ranges for evaluating the values of the parameters, and that compare to determine which one of the three ranges that the values of the parameters belong to each of the values of the parameters displayed in the list is contained in, and displays the values of the parameters so that a result of the comparison determination by identifying a result of the comparison determination and making it visually recognizable.

According to the second aspect, it is possible to recognize whether the value of the parameter at each phase is within the standard range, or exceeding or below the standard range, and also the tendency, and it becomes possible to recognize them as absolute values (as unmodified numerical values at the time of measurement) or relatively (with reference to the value of a parameter of a specified phase).

Further, in a third aspect of the present invention, in the ultrasonic imaging apparatus according to the second aspect: the evaluation display controller displays, as a result of the comparison and determination, one or a combination of a color or shape of characters representing the values of the parameters belonging to the respective ranges and a color, pattern or shape of a background of the characters so as to be differentiated for the ranges, thereby making it possible to identify and visually recognize.

Further, in a fourth aspect of the present invention, in the ultrasonic imaging apparatus according to the third aspect: the evaluation display controller performs the comparison and determination by standardizing the three of the over range, the standard range and the under range and, regarding the respective values of the parameters displayed in the list, for each of the types of the parameters, standardizing the value of the parameter in each of the examination stages with a value of a parameter in a specific examination stage.

In a fifth aspect of the present invention, in the ultrasonic imaging apparatus according to the fourth aspect: the list display controller displays one type of parameter so as to be selectable by the operation part when displaying the list of the values of the parameters; and the display controller further includes a graph generator configured to generate a graph showing change of the values of the parameters in the respective examination stages with respect to the parameter of the type selected with the operation part and control the display to display the graph.

Further, a sixth aspect of the present invention provides an ultrasonic imaging apparatus having: a data acquiring part configured to transmit ultrasonic waves to a subject and receive the reflected waves to obtain values of a plurality of types of parameters signifying a state of a site of the subject; and a controller configured to control the data acquiring part to acquire values of respective types of parameters by, in a plurality of types of stress echocardiographies, applying stress corresponding to one type or the plurality of types to the site in a plurality of examination stages for each of the types, and applying no stress in a normal examination, the ultrasonic imaging apparatus comprising: a storage configured to store the values of the respective parameters acquired by the data acquiring part in the stress echocardiographies so as to be identifiable by the types of the stress echocardiographies, by the types of the parameters, and by the examination stages; a display; an operation part; and a display controller having: a list display controller configured to, when a type of the stress echocardiography is designated through the operation part and a request for browsing an examination result is received, read out the values of the parameters of the designated type of stress echocardiography from the storage, and display a list of the values of the parameters on a graphic in which one item is the value of the parameters and the other item is each of the examination stages of the designated stress echocardiography; and a graph generator configured to generate a graph showing changes in the values of the parameters in the respective examination stages with respect to the parameter of the type selected with the operation part, and control the display to display the graph.

In a seventh aspect of the present invention, in the ultrasonic imaging apparatus according to the sixth aspect: the graph generator standardizes, regarding each of the values of the parameters of the selected types, for each of the types of the parameters, the value of the parameter in each of the examination stages by a value of a parameter in a specific examination stage, and plots the standardized values of the respective types on a single coordinate in which a vertical axis takes a magnitude of a parameter value with respect to a standard value and a horizontal axis takes the respective examination stages, thereby generating.

Further, in an eighth aspect of the present invention, in the ultrasonic imaging apparatus according to Claim 6: the graph generator plots, regarding the respective values of the parameters of the selected types, for each of the types of the parameters, each of the values of the parameters of the selected types on a coordinate in which a vertical axis takes a magnitude of a parameter value and a horizontal axis takes the respective examination stages, thereby generating.

Further, a ninth aspect of the present invention provides an ultrasonic imaging apparatus, comprising: a controller that follows an examination procedure of applying one type of stress or a plurality of types of stresses to a site of a subject in a plurality of examination stages for each of the types and conducting a plurality of types of stress echocardiographies for obtaining parameters signifying states of a plurality of types of sites at each of the examination stages, and an examination procedure of applying no stress and conducting a normal examination; a display; an operation part; a storage; a data acquiring part having: a measuring part configured to, when receiving from the controller an examination procedure of a stress echocardiography of the type designated with the operation part, transmit ultrasonic waves to the site, and receive the reflected waves to obtain the values of the plurality of types of parameters signifying the state of the site of the subject based on the received examination procedure; and a data management part configured to control the storage to store at least the values of the respective parameters acquired by the measuring part in the stress echocardiography, by assigning tags so as to be identifiable by the type of the designated stress echocardiography, the type of parameter, and by the examination stage; and a display controller having a list display controller configured to, when the type of the stress echocardiography finished in the past is designated through the operation part and a request for browsing the examination result is received, refer to the tags of the respective parameters stored in the storage to read out the values of the respective parameters in the respective examination stages of the designated type of stress echocardiography, and display a list of the values of the parameters on a graphic in which one item takes the types of the parameters and the other item takes the respective examination stages in the designated stress echocardiography.

Further, a tenth aspect of the present invention provides a stress echo browsing apparatus, comprising: a storage configured to store values of a plurality of types of parameters signifying a state of a site of a subject acquired by applying stress to the site in a plurality of examination stages and conducting a stress echocardiography with ultrasonic waves by an ultrasonic imaging apparatus with respect to each of the examination stages, so as to be identifiable by the type of the stress echocardiography, by the type of parameter, and by the examination stage of the stress echocardiography; a display; an operation part; and a display controller having a list display controller configured to, when the type of the stress echocardiography is designated through the operation part and a request for browsing the examination result is received, read out the values of the parameters of the designated type of stress echocardiography, and display a list of values of the parameters on a graphic in which one item takes the types of the parameters and the other item takes the respective examination stages in the designated stress echocardiography.

According to the tenth aspect, it becomes possible to use the result of examination in a stress echo browsing apparatus that does not have a measuring part.

BRIEF DESCRIPTION OF THE DRAWINGS

FIG. 1 is a diagram showing the functional configuration of an ultrasonic imaging apparatus according to an embodiment of the present invention.

FIG. 2 is a view for explaining the configuration of an examination procedure.

FIG. 3 is a view showing an example of a displayed list of parameter values.

FIG. 6 is a flowchart illustrating a series of measurement operations.

DETAILED DESCRIPTION OF THE PREFERRED EMBODIMENTS

Configuration

An ultrasonic imaging apparatus, a stress echo browsing apparatus, and a stress echo browsing program according to an embodiment of the invention will be described with reference to the drawings. FIG. 1 is a diagram showing the functional configuration of the ultrasonic imaging apparatus according to the present embodiment.

Figure 4:
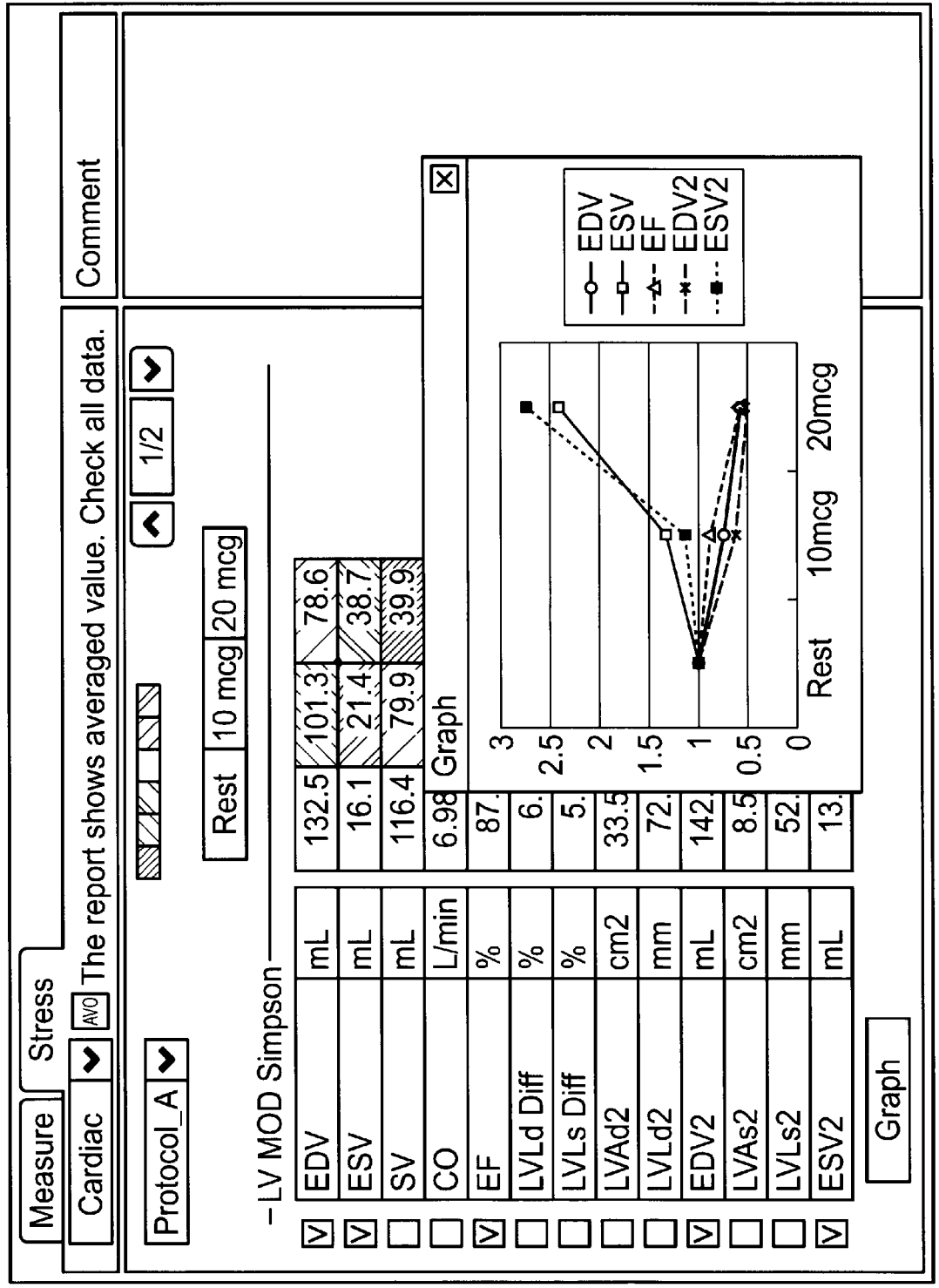
FIG. 4 is a view illustrating an example in graph display showing parameter value changes.
Figure 5:
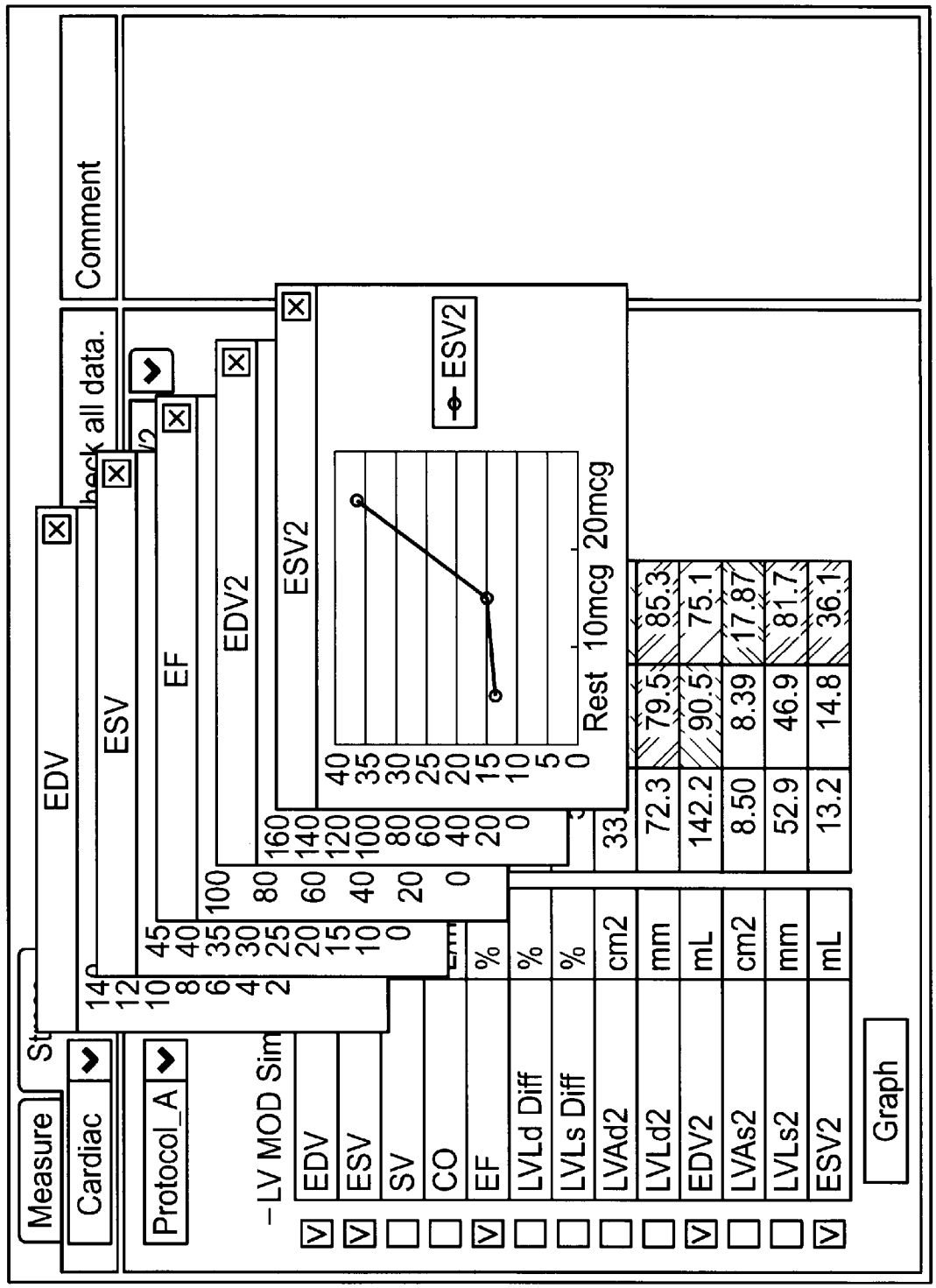
FIG. 5 is a flowchart showing a series of measurement operations using the ultrasonic imaging apparatus according to an embodiment of the present invention.

The stress echo browsing apparatus is included as part of FIG. 1, the stress echo browsing program is a program for implementing the execution functions of the stress echo browsing apparatus, and these functions will be described based on FIG. 1. FIG. 2 is a view for explaining the configuration of an examination procedure. FIG. 3 is a view showing an example of display of a list of parameter values. FIG. 4 is a view illustrating an example of graph display showing parameter value changes. FIG. 5 is a view showing another example of a graph display representing the change of parameter values. FIG. 6 is a flowchart illustrating a series of measurement operations.

In FIG. 1, a data acquiring part 100 includes a measuring part 50 and a data management part 9. Specifically, the measuring part 50 includes an ultrasound probe 2, a transmitter 3, a receiver 4, a parameter calculator 7, an image generator 11, and the data management part 9. The data acquiring part 100 is of a conventional art, except for the data management part 9. Furthermore, the data acquiring part 100 is controlled by a measurement controller 18. First, the conventional art will be described briefly.

The ultrasound probe 2 has an internally installed ultrasonic transducer (not illustrated) with a plurality of transducer cells integrated therein. The ultrasound probe transmits ultrasonic waves generated from the ultrasonic transducer into a subject 1 as an ultrasonic beam, and receives the reflected waves therefrom. In the ultrasound probe 2, in response to an instruction on transmission conditions received by the transmitter 3 from the measurement controller 18, a specified high-voltage pulse is sequentially applied to each of the transducer cells at a timing with a specified delay time in compliance with the transmission conditions, whereby each of the transducer cells is driven to generate an ultrasonic beam. On the other hand, each of the transducer cells of the ultrasonic transducer receives the reflected waves of the ultrasonic beam reflected from the inside of the subject 1, converts the reflected waves to electrical signals (hereinafter referred to as "received signals"), and transmits the signals to the receiver 4. The receiver 4 receives the received signals under receiving conditions instructed by the measurement controller 18 beforehand. In other words, the received signals received by the receiver 4 are subjected to gain correction by a preamplifier, and then subjected to A/D conversion. Data after the A/D conversion is temporarily written in or read out from a memory (not illustrated) via a bus at a required timing. Furthermore, after reading out the data from the memory, the receiver 4 executes phasing addition on the data, and transmits the data to a B-mode processor 5 or a Doppler processor 6 finally. The B-mode processor 5 and the Doppler processor 6, respectively, execute a process for B-mode image configuration and a process for Doppler-mode image configuration and transmit the processed image data to the image generator 11 in the display controller 200. At this moment, the processed image is stored in the image memory 11a. The image data used in the image generator 11 is temporarily stored in the image memory 11a so that various types of processes are executed thereon, and is read out or written in via the bus when necessary. Then, the data is converted to analog data by D/A conversion in the image generator 11, transmitted to the display controller 200, and displayed on a screen of the display 17 as an ultrasonic image.

On the other hand, an examination of a circulatory organ with the ultrasonic imaging apparatus requires specification of a cardiac time phase, storage of an image in the designated cardiac time phase, and storage of a moving image at a designated heart rate. Therefore, in order to acquire ECG signals, which constitute electrocardiographic information of a living body, the ultrasonic imaging apparatus is equipped with an ECG unit 19. An ECG attachment 20 connected to the ECG unit 19 is made into contact with the subject 1 of an examination target, subtle electric signals within the subject 1 are acquired by the ECG attachment 20, the ECG signals are amplified by an amplifier (not illustrated) of the ECG unit 19, and signals called R waves of particularly intense signals are detected. Data handled by each part is synchronized with the R waves. The amplified ECG signals are stored in the image memory 11a via the bus. After that, the measurement controller 18 executes synchronous control with the B-mode processor 5 and the Doppler processor 6, reads out a B-mode image and Doppler-mode image subjected to synchronization and the ECG signals from the image memory 11a, and synthesizes them in the image generator 11, and the display controller 200 controls the display 17 to display a synthesized image.

Accordingly, it is possible to acquire an image in which the respective images are temporally synchronized, e.g., an image at the timing of generation of the R waves. Moreover, the measurement controller 18 controls the storage of an image or the storage of a moving image based on the ECG signals in response to a request inputted by the user through the operation part 16.

The measurement controller 18 is composed of a program and a CPU for executing the program, and mainly executes the functions described in (1) and (2) below while comprehensively controlling the entire ultrasonic imaging apparatus.

(1) The measurement controller 18 has an examination protocol (hereinafter referred to as an "examination procedure") for causing the data acquiring part 100, etc., to perform an examination as shown in FIG. 2, and instructs each part according to the examination procedure selected (designated) by an operator through the operation part 16. In FIG. 2, a normal examination represents a case in which the shape of a site or the state of a blood flow velocity, etc. is measured without stressing the site. A stress echocardiography represents, as described already, an examination of measuring the state of a site in a state where the site is stressed. In the stress echocardiography, one of examination procedures A, B and C is executed based on an instruction through the operation part 16. The examination procedure A, the examination procedure B and the examination procedure C are set separately depending on the type of a load applied to the site, the manner of application, the method of measurement, etc. For example, as described above, the procedures are divided in accordance with the exercise load and the dobutamine stress. Furthermore, measurement procedures are separately created for each of the examination procedures according to the order of applying a load to the site, that is, the order of phases. Then, after each phase is designated through the operation part 16, the parameter calculator 7 is caused to calculate the parameters signifying the state of the site by analyzing the images measured in the phase.

(2) Classification tags are generated and transmitted to the data management part 9.

When the type of an examination and the phase are designated through the operation part 16, the measurement controller 18 executes the control (1) described above, transmits, to the data management part 9, tags for classifying a normal examination or stress echocardiography as described above and tags for indicating the phase, and assigns the tags to the respective parameter values calculated by the parameter calculator 7.

For example, as shown in FIG. 2, when an instruction to execute the normal examination is received, tag "00" is generated. When an instruction to execute the stress echocardiography is received, the examination procedure and the phase are designated. If an instruction of the stress echocardiography, the examination procedure B and the phase 1 is received, "B1" (B indicates the examination procedure B of the stress echocardiography, and "1" indicates the phase) is generated.

When the phase is designated, the parameter calculator 7 executes measurement and calculates the parameters. As described later, the calculation of the parameters is performed through execution of application software for calculating parameters. Since the parameter calculator recognizes which type of parameter is calculated by itself, the parameter calculator assigns one of tags P1, P2, . . . representing the type of parameter recognized by itself to the calculated parameter value, and transmits to the data management part 9.

The data management part 9 combines the classification tag received from the measurement controller 18 and the classification tag indicating the type of parameters received from the parameter calculator 7, and stores into the storage 10. For example, when a tag P1 indicating the type is received together with the value of a parameter from the parameter calculator 7, and if a classification tag received from the measurement controller 18 is B1, a classification tag "B1-P1" is generated and assigned to the value of the parameter. In FIG. 2, as described above, among the tags, A1-An, B1-Bm and C1-Ck are classifications of the type of an examination, a measurement procedure and a phase, whereas P1, P2 . . . are tags for classifying the type of a parameter.

(3) Transmission and reception conditions of the transmitter and receiver are controlled.

At the time of measurement in each phase, the measurement controller 18 controls data-processing conditions at the time of transmission/reception of the transmitter 3 and the receiver 4, such as a repetition cycle at the time of transmission, the intensity of an ultrasonic beam, a delay at the time of transmission, a delay at the time of reception, and phasing. They may be stored beforehand as a control plan, or may be controlled in a corrected control plan in response to an instruction to correct the stored control plan through the operation part 16.

In FIG. 1, the parameter calculator 7 receives image data of a site of a measurement target from the B-mode processor 5 and/or the Doppler processor 6, and calculates parameters signifying the state of the site. There are various types of parameters signifying the state of the site, and typical examples thereof are the length and area of the site, the velocity and time of change of the site, and the like.

As described above, the parameter calculator 7 has various types of applications software that calculate parameters signifying the state of a site of a measurement target from image data, and executes them by the CPU, thereby achieving its functions. In other words, the parameter calculator calculates the values of the parameters by protocols of the respective applications, and transmits the values of the parameters with the types of parameters specified by the applications software, to the data management part 9. The parameter calculation is executed by the applications software, but not all of them are performed automatically. Operator's tasks, such as designation of the range of an area obtained from a curve line on a displayed image by using the operation part 16 and the display 17 to obtain the parameters of the area, are included. The parameter-calculating function itself is the same technique as in JP-A 2006-26151 and is a prior art, so a description thereof is omitted.

As described in (2), the data management part 9 causes the storage 10 to store with the classification tag received from the measurement controller 18 and the tag indicating the type of parameter received from the parameter calculator 7. In FIG. 1, the parameter calculator 7 and the data management part 9 are shown as separate blocks, but they may be shown in the same block. For example, after a program of calculating a parameter value of each application software for calculating each type of parameter, a command to assign a tag "X-P1" obtained by synthesizing a variable X (a classification tag to be received from the measurement controller 18) and the type of a parameter calculated by the parameter calculator 7 (e.g., "P1") to the calculated parameter value is written. After the calculation of the parameter value, based on a variable value X=B1 indicating a phase actually received from the measurement controller 18, it is possible to assign the "X-P1" tag as a tag "B1-P1." In the normal examination, a variable value X=00 is received, and a tag "00-P1" can be assigned.

Therefore, the storage 10 stores so as to be identifiable by tags by the types of examinations such as the normal examination and stress echocardiography and, in the case of the stress echocardiography, by the types of stress echocardiographies (by the examination procedures), by the phases, and by the types of parameters. The storage 10 may also serve as the image memory 11*a*.

In FIG. 1, the display controller 200 includes a list display controller 12, an evaluation display controller 13, a graph generator 14, and an interface controller 15. The interface controller 15 composes a user interface together with the operation part 16 and the display 17, and works as an interface of information among the internal configuration, the operation part 16 and the display 17. For example, when a table with a list of a plurality of items is displayed on the display 17, a marker becomes settable on a desired item, the item is selected by setting (or clicking) a determination key with the operation part 16, and the selected item is transmitted to the internal main part.

In the description of the operation of each part in the present embodiment, the description of the interface controller 15 in the exchange of information between each part and the operation part 16, etc., will be omitted.

Receiving a request for displaying a list, designation of the examination type, whether the normal examination or the stress examination, and designation of the type of stress echocardiography (the type of examination procedure in FIG. 2) from the operation part 16, the list display controller 12 searches in the storage 10, reads out the parameter value of a tag matching each designation, embeds the value of the read-out parameter in a prepared list display format, and controls the display part 17 to display. The values of parameters are displayed so as to be embedded in the corresponding items in a format of a coordinate space in which the items in the vertical direction take the types of parameters and the items in the horizontal direction are the phases in order. An example thereof is shown in FIG. 3. In FIG. 3, "Measure" indicates a normal display tag 001 (equivalent to a tag indicating the normal examination in FIG. 2). "Stress" is a stress echo display tag 002 (a tag indicating the stress echocardiography in FIG. 2).

In FIG. 3, the "Stress" is selected and instructed, and "Protocol A" (equivalent to the examination procedure A in FIG. 2) is selected and designated from a protocol selection pull-down menu 003 for stress echo. "Rest," "10 mcg" and "20 mcg" in the horizontal direction represent Phase 005, and are equivalent to Phase A1, Phase A2 and Phase A3 in FIG. 2, respectively (m=3). The vertical axis in FIG. 3 indicates items representing the parameter types with symbols and also indicates the units of the parameter values. For example, EDV indicates the volume of the left ventricle in the diastolic phase, ESV indicates the volume in the systolic phase, SV indicates EDV−ESV, and EF (Ejection Fraction) indicates (SV/EDV)×100. In a measurement value display area 007 in FIG. 3, the values of the corresponding parameters are displayed.

The evaluation display controller 13 has, for each of the parameter types, a threshold in which a range including the parameter value of a phase designated by the operation part 16 is a standard range, a threshold for one or a plurality of ranges in a direction toward greater values than that of the standard range, and a threshold for one or a plurality of ranges in a direction toward smaller values than that of the standard range. The evaluation display controller compares the parameter value of each phase with the thresholds to determine the range to which the parameter value belongs, and displays so that the belonging range can be visually recognized and identified from the other ranges. In this identification display, the evaluation display controller 13 displays so that one of or a combination of the color or shape of characters representing the parameter value of the belonging range by the comparison and determination, or the color, pattern or shape of the background of the characters are differentiated for every range. In an example of this display, when the aforementioned list is displayed on the display 17, a column where the relevant parameter value is displayed so as to be filled with a color (or a pattern or a sign) for identifying the range to which the value belongs. This example is shown in FIG. 3. FIG. 3 is a view of displaying the list as described above. In FIG. 3, the range to which the parameter value of "Rest" of the Phase 1 belongs is the standard, and each parameter value is displayed with a color for the range to which the parameter belongs (FIG. 3 shows with patterns instead of colors, because colors cannot be used in the drawings for application). The belonging ranges of the parameters (in FIG. 3, the parameters are divided into six ranges; it is preferable there are at least three ranges, i.e., standard, under and over) and the color coding are shown in a color bar 004 indicating the ratio of change of the measured values, in the upper part in the middle of FIG. 2. Therefore, it is possible to directly recognize the degree of change by the difference in color, as compared with the value of the parameter of Phase 1. Furthermore, a specific example of the identification display may be such that the color for the standard value is set to black, a gradual change toward brighter colors in a warm color group is made for increasing values from the standard value, whereas a gradual change toward brighter colors in a cold color group is made for decreasing values.

The values of the parameters in FIG. 3 are shown how they have been calculated, that is, in absolute values, but the determination of a range to which a parameter belongs may be made with relative comparison by standardizing each range with a standard range while also standardizing the value of each parameter with the parameter value of a designated phase by dividing the former by a parameter value for each phase.

In FIG. 3, Phase 1 "Rest" is designated as a standard for comparison, but any other phase such as 2 and 3 may be designated by the operation part 16.

Receiving, from the operation part 16, a request for displaying a graph, designation of the examination type, whether the normal examination or the stress examination, designation of the type of stress echocardiography (the type of examination procedure in FIG. 2), and designation of the type of parameter, the graph generator 14 searches in the storage 10, reads out the parameter values of tags matching the respective designations, plots the values of the respective parameters on a coordinate taking the order of phases on the horizontal axis and the magnitude of each parameter value on the vertical axis, and causes the display 17 to display the graph. With reference to FIGS. 3, 4 and 5, when the parameters of types checked through the operation part 16 in a check box 006 for selecting measurement parameters for graph display provided at the left end of the respective parameter items in the list display of FIG. 3 are selected, the graph generator 14 generates a graph of the parameters. The graph generator 14 may be configured to be capable of executing independently from the list display controller 12, etc.

FIG. 4 shows an example of the graph. When EDV, ESV, EF, EDV2 and ESV2 are selected in the check box and a "Graph" key at the bottom is clicked, a graph created by the graph generator 14 is displayed so as to be overlapped on the list display. In this graph, the horizontal axis takes the order of phases and the vertical axis takes the magnitude of a proportion (a ratio value) when the value of each parameter of each phase is standardized by the parameter value of the Phase 1

(the proportion may be displayed in percentages). In this case, the change in parameters of each type can be visually recognized on the same coordinate. In FIG. 5, the values of the parameters are not standardized and are displayed by the magnitude of the absolute values thereof. Therefore, the graph generator 14 generates graphs for the respective types of the designated parameters. The standardization may be performed by such a method that the difference between the value of the parameter of Phase 1 and the value of a parameter of each phase are divided by the value of the parameter of Phase 1.

(Operation)

Next, a series of operations for measurement will be described with reference to FIG. 6. Part of the description may overlap with a description of the configuration and operation.

(Step S1)

After the power is turned on, the display controller 200 controls the display 17 to display an operational guidance for an examination, and selection by the operator is waited.

(Step S2)

The operator selects the type of an examination. If the examination is stress echocardiography, the operator also selects an examination procedure. The transmission and reception conditions, etc., of the measuring part 50 are sometimes inputted and set.

(Step S3)

In the case of a stress examination, Step S4 is executed, whereas in the case of not a stress examination, a normal examination in Step 10 is executed.

(Step S4)

In a case where the examination is stress echocardiography, a guidance screen of the phase is displayed. When an examination procedure of the stress examination is selected, the number m of phases is also determined.

(Step S5)

The operator selects the phase. First, the operator selects phase k=1.

(Step S6, S7)

The data acquiring part 100 executes the examination of Phase 1.

At this moment, the operator executes regulation and change of load appropriate for the phase, and also inputs information (for example, the range of a site to calculate the volume) necessary for execution of the measurement through the operation part 16.

(Step S8)

The data management part 9 assigns a classification tag to the value of each parameter measured and calculated by the data acquiring part 100 so that it is possible to specify by the selected examination type, the type of the examination procedure, the phase and the type of the calculated parameter, and causes the storage 10 to store.

(Step S9)

The measurement controller 18 determines whether the present phase order k coincides with the planned phase number m. If it does not coincide, the operation goes back to step S4, and examinations of the total phase number are performed until k=m is achieved.

(Step 10)

If the normal examination is selected, the measurement controller 18 executes the examination based on the examination procedure for the normal examination. After execution, a classification tag is assigned to the calculated value of each parameter, and stored.

However, in this case, Step S9 is passed (k=m=1).

(Step S11)

The measurement controller 18 ends the examination when the examination is finished for all the phases.

Judging from the above configuration and operation, the present embodiment is configured so that parameters signifying the state of a site are classified and stored upon acquisition, so that it is possible to read out and display at any time after measurement is finished. Since a variation of the state from the standard can be displayed as a graph, it is possible to grasp the variation directly and quantitatively.

Accordingly, for example, in the diagnosis of a cardiac function, it is possible to prevent overlooking, and it is also possible to evaluate qualitatively, quantitatively and efficiently. Furthermore, the efficiency in diagnosis may be increased.

What is claimed is:

1. An ultrasonic imaging apparatus, comprising:
   a data acquiring part configured to transmit ultrasonic waves to a subject and receive reflected waves to obtain values of a plurality of types of parameters signifying a state of a site of the subject;
   a controller configured to control the data acquiring part to acquire values of respective types of parameters under conditions that, in a plurality of types of stress echocardiographies, a stress is applied corresponding to one type or the plurality of types to the site through administering medication or exercise, while no stress is applied in a normal examination;
   a storage configured to store the respective parameter values acquired by the data acquiring part in the stress echocardiographies so as to be identifiable by the types of the stress echocardiographies, by the types of the parameters, and by the examination stages;
   a display;
   an operation part; and
   a display controller comprising
      a list display controller configured to, when a type of the stress echocardiography is designated through the operation part and a request for browsing an examination result is received, read out the values of the parameters of the designated type of stress echocardiography from the storage, and display a list of the values of the parameters in parallel in order of the examination stages on a two-dimensional screen in which one dimension is the types of the parameters and the other dimension is the plurality of examination stages of the designated stress echocardiography, allowing one type of the parameters to be selected through the operation part; and
      a graph generator configured to normalize the parameter whose type is selected by the operation part based on a parameter at a specific examination stage, to generate a graph indicating a change of the normalized parameter at each examination stage, and to cause the display to display the generated graph.

2. The ultrasonic imaging apparatus according to claim 1, wherein:
   the display controller includes an evaluation display controller that stores, for each of the types of the parameters, at least three of a standard range, an over range exceeding the standard range, and an under range below the standard range as ranges for evaluating the values of the parameters, and that performs a comparison to determine a range containing each of the values of the parameters displayed in the list from among the three ranges to which the values of the parameters belong, and displays the values of the parameters in a manner that a result of the comparison determination can be identified and visually recognized.

3. The ultrasonic imaging apparatus according to claim 2, wherein:
the evaluation display controller displays, as a result of the comparison and determination, one or a combination of a color or shape of characters representing the values of the parameters belonging to the respective ranges and a color, pattern or shape of a background of the characters so as to be differentiated for the ranges, thereby making it possible to identify and visually recognize.

4. The ultrasonic imaging apparatus according to claim 3, wherein:
the evaluation display controller performs the comparison and determination by standardizing the three of the over range, the standard range and the under range and, regarding the respective values of the parameters displayed in the list, for each of the types of the parameters, standardizing the value of the parameter in each of the examination stages with a value of a parameter in a specific examination stage.

5. The ultrasonic imaging apparatus according to claim 4, wherein
the list display controller displays one type of parameter so as to be selectable through the operation part when displaying the list of the values of the parameters.

6. The ultrasonic imaging apparatus according to claim 1, wherein
the graph generator is configured to generate, by plotting, regarding the respective values of the parameters of the selected type, for each of the types of the parameters, each of the values of the parameters of the selected type on a coordinate in which a vertical axis takes a magnitude of a parameter value and a horizontal axis takes the respective examination stages.

7. The ultrasonic imaging apparatus of claim 1, wherein the list display controller is further configured to allow the specific examination stage used to normalize the parameters to be selected through the operation part.

8. An ultrasonic imaging apparatus, comprising:
a controller that follows an examination procedure in which one type of stress or a plurality of types of stresses is applied to a site of a subject through administering medication or exercise and conducting a plurality of types of stress echocardiographies for obtaining parameters signifying states of a plurality of types of sites at each of the examination stages, and an examination procedure in which no stress is applied and conducting a normal examination;
a display;
an operation part;
a storage;
a data acquiring part including a measuring part configured to, when receiving from the controller an examination procedure of a stress echocardiography of the type designated through the operation part, transmit ultrasonic waves to the site, and receive reflected waves to obtain the values of the plurality of types of parameters signifying the state of the site of the subject based on the received examination procedure; and a data management part configured to control the storage to store at least the values of the respective parameters acquired by the measuring part in the stress echocardiography, by assigning tags so as to be identifiable by the type of the designated stress echocardiography, by the type of parameter, and by the examination stage; and
a display controller comprising
a list display controller configured to, when the type of the stress echocardiography finished in the past is designated through the operation part and a request for browsing the examination result is received, refer to the tags of the respective parameters stored in the storage to read out the values of the respective parameters in the respective examination stages of the designated type of stress echocardiography, and display a list of the values of the parameters in parallel in order of the examination stages on a two-dimensional screen in which one dimension is the types of the parameters and the other dimension is the plurality of examination stages in the designated stress echocardiography, allowing one type of the parameters to be selected through the operation part; and
a graph generator configured to normalize the parameter whose type is selected by the operation part based on a parameter at a specific examination stage, to generate a graph indicating a change of the normalized parameter at each examination stage, and to cause the display to display the generated graph.

9. A stress echo browsing apparatus, comprising:
a storage configured to store values of a plurality of types of parameters signifying a state of a site of a subject acquired under conditions that a stress is applied to the site through administering medication or exercise and conducting a stress echocardiography with ultrasonic waves by an ultrasonic imaging apparatus with respect to each of the examination stages, so as to be identifiable by the type of the stress echocardiography, by the type of parameter, and by the examination stage of the stress echocardiography;
a display;
an operation part; and
a display controller comprising
a list display controller configured to, when the type of the stress echocardiography is designated through the operation part and a request for browsing the examination result is received, read out the values of the parameters of the designated type of stress echocardiography, and display a list of values of the parameters in parallel in order of the examination stages on a two-dimensional screen in which one dimension is the types of the parameters and the other dimension is the plurality of examination stages in the designated stress echocardiography, allowing one type of the parameters to be selected through the operation part; and
a graph generator configured to normalize the parameter whose type is selected by the operation part based on a parameter at a specific examination stage, to generate a graph indicating a change of the normalized parameter at each examination stage, and to cause the display to display the generated graph.

* * * * *